US010258562B2

(12) United States Patent
Opawale et al.

(10) Patent No.: US 10,258,562 B2
(45) Date of Patent: Apr. 16, 2019

(54) EFFERVESCENT TABLET CONTAINING HIGH LEVEL OF ASPIRIN

(71) Applicant: Bayer HealthCare LLC, Whippany, NJ (US)

(72) Inventors: Foyeke Opawale, Flemington, NJ (US); Priya Nayak, Ringoes, NJ (US); Gerard Meisel, Budd Lake, NJ (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

(21) Appl. No.: 15/032,054

(22) PCT Filed: Oct. 23, 2014

(86) PCT No.: PCT/US2014/061874
§ 371 (c)(1),
(2) Date: Apr. 25, 2016

(87) PCT Pub. No.: WO2015/061521
PCT Pub. Date: Apr. 30, 2015

(65) Prior Publication Data
US 2016/0263015 A1 Sep. 15, 2016

Related U.S. Application Data

(60) Provisional application No. 61/894,740, filed on Oct. 23, 2013.

(51) Int. Cl.
*A61K 9/00* (2006.01)
*A61K 9/46* (2006.01)
*A61K 47/02* (2006.01)
*A61K 31/375* (2006.01)
*A61K 31/60* (2006.01)

(52) U.S. Cl.
CPC .......... *A61K 9/0007* (2013.01); *A61K 9/0009* (2013.01); *A61K 31/375* (2013.01); *A61K 31/60* (2013.01); *A61K 47/02* (2013.01)

(58) Field of Classification Search
None
See application file for complete search history.

(56) References Cited

U.S. PATENT DOCUMENTS

| 3,105,792 | A | * | 10/1963 | White | A61K 9/0007 424/44 |
| 3,773,922 | A | * | 11/1973 | Gergely | A61K 9/0007 424/44 |
| 4,083,950 | A | | 4/1978 | Duvall et al. | |
| 4,491,574 | A | | 1/1985 | Seifter et al. | |
| 5,723,453 | A | * | 3/1998 | Phykitt | A61K 9/0095 424/44 |
| 5,770,215 | A | | 6/1998 | Moshyedi | |
| 5,859,053 | A | * | 1/1999 | Lesur | C07C 203/04 514/509 |
| 6,479,551 | B1 | * | 11/2002 | Plachetka | A61K 9/0007 424/451 |
| 2011/0300216 | A1 | * | 12/2011 | First | A61K 9/0056 424/466 |
| 2015/0352129 | A1 | * | 12/2015 | Habboushe | A61K 31/616 424/472 |

FOREIGN PATENT DOCUMENTS

EP 0377906 A2 7/1990

OTHER PUBLICATIONS

Rote, Liste, Aspirin Plus C, Mar. 13, 2008, International Search Report dated Jan. 12, 2015.
"International Search Report for International Application No. PCT/US2014/061874 dated Jan. 27, 2015".
Mason, W., "Kinetics of Aspirin Absorption Following Oral Administration of Six Aqueous Solutions with Different Buffer Capacities", J. Pharma Sci, 1984, 73(9), 1258-61.
Mason W.D. & Winer, N., "Kinetics of Aspirin, Salicylic Acid, and Salicyluric Acid, and Salicyluric Acid following Oral Administration of Aspirin as a Tablet and Two Buffered Solutions", J. Pharm Sci., Aug. 21, 1980, 70(3), 262-265.

* cited by examiner

Primary Examiner — Susan T Tran

(57) ABSTRACT

The present invention relates to a single-layer, effervescent tablet comprising a high level of aspirin and a reduced amount of alkaline substances, where the tablet rapidly dissolves in water.

12 Claims, 3 Drawing Sheets

EFFERVESCENT TABLET CONTAINING HIGH LEVEL OF ASPIRIN

FIELD OF THE INVENTION

This invention relates to effervescent formulations containing high amounts of aspirin, and to methods of making and using these formulations.

BACKGROUND OF THE INVENTION

Aspirin is one of the most recognized medicines in the world. The benefits of aspirin for pain, inflammation, and heart health have caused some writers to suggest that it may be the most successful over-the-counter medicine in history. Aspirin has been marketed in many different delivery systems, including compressed tablets (e.g., Bayer® aspirin tablets), powders (BC® and Goody's® powders), and effervescent tablets (Alka-Seltzer® tablets).

Aspirin has been combined with different active ingredients, including caffeine (Anacin® tablets) and acetaminophen (Excedrin® tablets), and it has been combined with various buffers (Bufferin®, Ascriptin®, and Bayer® Plus tablets).

Aspirin has also been proposed for use in combination with various vitamins and minerals, such as in U.S. Pat. No. 4,491,574 (vitamin A) and U.S. Pat. No. 5,770,215 (multivitamins). One formulation that has proved to be commercially successful is the combination of aspirin and ascorbic acid ("vitamin C") in an effervescent tablet (Aspirin® Plus C), which was introduced in Europe over thirty years ago. Current dosing for Aspirin® Plus C is one to two tablets, with each tablet containing 400 mg aspirin and 240 mg vitamin C.

Despite aspirin's long history of success, it suffers from some manufacturing drawbacks. Aspirin is very hygroscopic and degrades quickly in a humid environment.

One method that one skilled in the art might employ to reduce the vulnerability of aspirin to degradation is to form a tablet having two or more layers, with aspirin in one layer and acidic or basic ingredients in another layer. These tablets require special handling and are more expensive to make than single layer tablets, and it can be difficult to ensure that the separate active ingredients are present at the proper levels in the tablet.

Effervescent formulations typically contain, in addition to one or more active ingredients, an acid source and a carbonate or hydrogen carbonate salt as the principal components of an effervescent couple. Prior efforts in formulating effervescent tablets containing aspirin have required excess amounts of alkaline substances, such as sodium carbonate, sodium bicarbonate, or sodium citrate to provide a highly soluble composition in water. This results in increased levels of elemental sodium, which can be problematic for individuals who should reduce their sodium intake.

A single-layer, effervescent tablet has long been needed that can provide a high level of aspirin and rapidly dissolve in water, without requiring excess amounts of alkaline substances.

SUMMARY OF THE INVENTION

The principal object of the invention therefore is to provide a single-layer, effervescent tablet comprising a high level of aspirin and a reduced amount of alkaline substances, where the tablet rapidly dissolves in water.

Incorporating a high level of aspirin into a single-layer tablet requires decreasing the amount of alkaline substances and/or buffering agent, relative to two tablets of the commercially available formulation, in order to provide a tablet that is acceptable to consumers and can utilize existing manufacturing equipment. It was believed that reducing the amount of one component of the effervescent couple would result in a longer tablet disintegration time. Unexpectedly, it was found that increasing the ratio of acidic to basic components enhanced dissolution of the aspirin.

According to one embodiment of the present invention, the effervescent tablet contains from about 600 to about 1000 mg of aspirin, about 1400 to about 2000 mg of alkaline substances, and about 240 to about 600 mg of vitamin C. One preferred embodiment contains about 800 mg of aspirin, about 1600 mg of alkaline substances, and about 480 mg of vitamin C. Preferably, the tablets of the present invention dissolve in water within about 5 minutes.

Another object of the invention is to provide a single-layer, effervescent aspirin tablet comprising a high level of aspirin, where the tablet has an acid neutralizing capacity ("ANC") of from about 10 mEq to about 24 mEq. Preferably, the ANC is from about 13 mEq to about 18 mEq. One preferred embodiment has an ANC of about 15 mEq.

The prior art suggests that ANC, or buffering capacity, plays a large role in intestinal absorption of aspirin. See Mason, W. D. & Winer, N. (1981). *J. Pharm. Sci.*, 70(3), 262-65; Mason, W. D. (1984). *J. Pharm. Sci.*, 73(9), 1258-61. Therefore, it was expected that decreasing the amount of the buffering agent present in two tablets of the commercially available formulation, and thereby reducing ANC, would adversely impact bioavailability. However, it was surprisingly found that embodiments of the present invention could have a decreased ANC and yet be bioequivalent to two tablets of the commercially available formulation.

A third object of the invention is to provide a single-layer, effervescent aspirin tablet comprising a high level of aspirin, where the tablet has an acid to base ratio (excluding APIs) of from about 1:1.2 to about 1:6. Preferably, the acid to base ratio is from about 1:3 to about 1:4. One preferred embodiment has an acid to base ratio of about 1:3.

A fourth object of the invention is to provide a single-layer, effervescent aspirin tablet comprising a high level of aspirin and free of sodium carbonate. Surprising it was found that absence of sodium carbonate had a positive impact on stability of the tablets of the present invention.

Preferably, tablets of the present invention have a weight of less than about 3600 mg and a thickness of not more than 4.6 mm. The pH of the tablets in an aqueous solution is preferably from about 5.8 to 6.8.

Additional objects and advantages of the invention will be set forth in part in the description that follows, and in part will be obvious from this description, or may be learned by practice of the invention. The objects and advantages of the invention may be realized and attained by means of the instrumentalities and combinations particularly pointed out in the appended claims.

DETAILED DESCRIPTION OF THE PREFERRED EMBODIMENTS OF THE INVENTION

Reference will now be made in detail to preferred embodiments of the invention.

As used herein, the term "high level of aspirin" means more than about 600 mg of aspirin in a single tablet, and preferably about 800 mg of aspirin in a single tablet.

Preferably, the amount of aspirin in a tablet containing a high level of aspirin should be no more than about 1000 mg of aspirin. This limit, however, is not a technological limit; 1000 mg is about the maximum recommended dosage permitted in many countries.

As used herein, the term "reduced amount of alkaline substances" means less than about 2700 mg of alkaline substances in a single tablet, preferably less than about 2000 mg. More preferably, a single tablet may contain from about 1400 to about 2000 mg of alkaline substances. For example, in one embodiment, a single tablet contains about 1600 mg of alkaline substances.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 5% of the particular term.

The tablet of the invention may comprise additional active ingredients, such as vitamin C, phenylephrine hydrochloride, pseudoephedrine hydrochloride, caffeine, or other NSAIDs. For example, the tablet may contain from about 240 to about 600 mg of vitamin C. Particularly preferred is the addition of about 480 mg of vitamin C in a single tablet.

EXAMPLES

Figure 1:
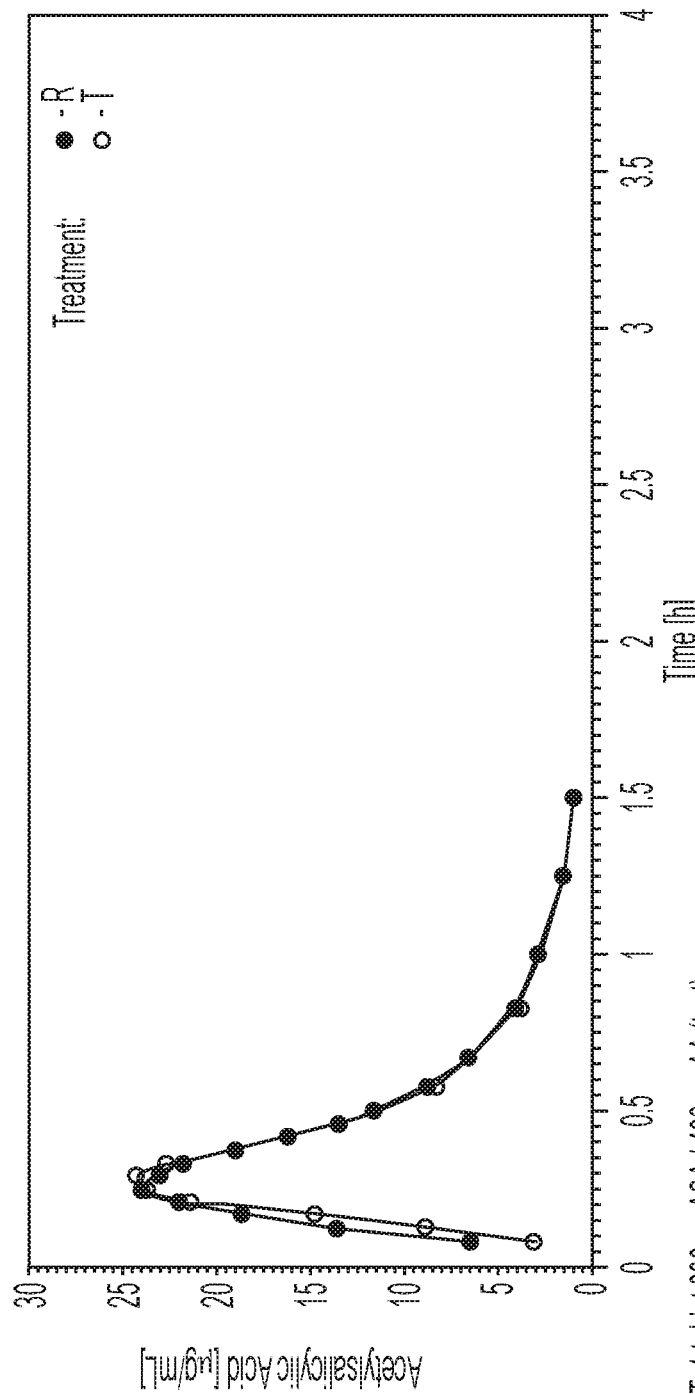
FIG. 1 is a chart showing mean plasma concentration of acetylsalicylic acid following administration of an effervescent tablet according to the present invention ("T") compared with the commercially available combination of aspirin and vitamin C (Aspirin® Plus C) ("R").

Powder blends were either produced by mixing in a V-blender or mixed manually during development. Preparation of samples was carried out in an environmental area of controlled temperature and low relative humidity, to eliminate the premature initiation of an effervescent reaction, due to uptake of moisture by the raw materials.

Aspirin

Aspirin (ASA) having a particle size specification of ($D_{50}$ 10-25 microns) was used. The API complies with the Ph. Eur, Ph. Jap. and USP specifications.

Ascorbic Acid

Ascorbic acid was used as supplied from vendor, that is, without milling. It complies with Ph. Eur and USP specifications.

Sodium Bicarbonate

Sodium bicarbonate was heat treated to convert the outer particle surface to sodium carbonate (calcination process)

The advantage of heat treatment is that early effervescent reaction is prevented should the product be exposed to moisture in the atmosphere. In addition, it was observed through tablet thickness measurements that using calcined sodium bicarbonate rather than a combination of plain sodium bicarbonate with sodium carbonate minimized tablet thickness.

Povidone

Micronization of ASA particles results in higher surface area and a tendency to aggregate to minimize the surface free energy. A hydrophilic polymer such as povidone adheres to the particle surface minimizing the aggregation due to hydrophobic interaction. Particle stabilization of the milled ASA was seen during disintegration tests in which less particle aggregation was observed on the water surface with prototypes made with povidone as compared to prototypes without this polymer.

Preliminary Studies

Each tablet of the commercial product Aspirin® Plus C contains 400 mg aspirin and 240 mg vitamin C, as well as effervescent components that include sodium hydrogen carbonate, anhydrous sodium carbonate, and citric acid.

Samples were prepared doubling the amounts of the ingredients in Aspirin® Plus C to produce a single tablet having a full, effective dose of 800 mg aspirin. These tablets, however, proved to be unacceptable for commercial production because the tablets were too thick. In general, a tablet weight of about 3,000 mg to about 3,500 mg is desired for existing manufacturing equipment.

Samples were next prepared as shown in Table 1 to evaluate the impact of eliminating or reducing the effervescent components, sodium citrate and sodium carbonate, from the tablets to reduce the tablet size. The acid neutralizing capacity (ANC) of the tablets was measured and compared to the ANC of the commercial formulation to see if the new tablets were able to provide the same benefit as the commercial formulation and to see if an ANC of at least 15 mEq was obtained, which is the approximate value required to ensure that the pH of the stomach fluid increased enough after ingestion to ensure dissolution of aspirin in the stomach environment.

TABLE 1

| | Prototypes | | |
|---|---|---|---|
| | Aspirin Plus C | Ex. 1 | Ex. 2 |
| Components removed | N/A | Sodium citrate | Sodium citrate; Sodium carbonate |
| ANC | 23.6 mEq | 25.5 mEq | 18.6 mEq |
| Acid to base ratio | 1.3:1 | 1:4.6 | 1:3.8 |
| Aqueous solution pH | 5.4 | 6.7 | 6.4 |

Eliminating sodium citrate from the combined formulation had little impact on ANC, but the absence of sodium citrate did affect the aqueous solution pH upon disintegration. The pH increased from 5.4 to 6.7, indicating that sodium citrate functions as a buffering agent. Removing sodium carbonate did affect ANC, which decreased to 18.6 mEq. The pH of the disintegration solution was determined to be 6.3. The two prototypes were calculated to have acid to base ratios (excluding APIs) of 1:4.6 and 1:3.8, respectively. In comparison, the acid to base ratio (excluding APIs) of the commercial product is 1.3:1.

Examples 3-14

Additional Examples were prepared as shown in Table 2 to evaluate the effect of lower acid to base ratios, targeting the ratio of Aspirin® Plus C (1.3:1). These examples showed prolonged disintegration time (DT) even though the pH range (5.1-5.4) was similar to the commercial product. It was also observed that the low acid to base ratio prototypes translated to lower ANC and pH values.

TABLE 2

(mg/effervescent tablet)

| Ingredients | Ex. 3 | Ex. 4 | Ex. 5 | Ex. 6 | Ex. 7 | Ex. 8 | Ex. 9 |
|---|---|---|---|---|---|---|---|
| ASA micronized, $D_{50}$ 10-25 micron | — | — | 800 | 800 | 800 | 800 | 800 |
| ASA micronized/Sodium Carbonate | 1067 | 1067 | — | — | — | — | — |
| Ascorbic Acid | 480 | 480 | 480 | 480 | 480 | 480 | 480 |
| Calcined Sodium Bicarbonate | 818 | 818 | 820 | 1085 | 1250 | 585 | 564.5 |
| Citric Acid Anhydrous | 835 | 835 | 835 | 835 | 520 | 900 | 941 |
| Sodium Carbonate | — | — | 265 | — | — | 585 | 564.5 |
| Potassium Bicarbonate | — | — | — | — | 300 | — | — |
| Docusate Sodium/Sodium Benzoate 85/15% | — | 15 | 15 | 15 | 1.750 | — | — |
| Colloidal Silicon Dioxide | — | — | 15 | 15 | — | 4 | 4 |
| Povidone | — | — | — | — | 1.750 | 17.5 | 17.5 |
| Total tablet weight | 3200 | 3215 | 3230 | 3230 | 3353.5 | 3371.5 | 3371.5 |
| Acid Neutralizing Capacity (ANC) | Not Determined | 9.41 | 10.11 | 7.41 | Not Determined | 10.8 | Not Determined |
| Acid to base ratio | 1:1.3 | 1:1.3 | 1:1.3 | 1:1.3 | 1:1.3 | 1:1.3 | 1:1.2 |
| Disintegration Time | <2 min | >5 min | >10 min | >10 min | >3 min | >3 min | — |
| pH | 5.259 | 5.125 | 5.188 | 4.893 | 6.19 | 5.371 | — |

| Ingredients | Ex. 10 | Ex. 11 | Ex. 12 | Ex. 13 | Ex. 14 |
|---|---|---|---|---|---|
| ASA micronized, $D_{50}$ 10-25 micron | 800 | 800 | 800 | 800 | 800 |
| ASA micronized/Sodium Carbonate | — | — | — | — | — |
| Ascorbic Acid | 480 | 480 | 480 | 480 | 480 |
| Calcined Sodium Bicarbonate | 585 | 621 | 621 | 621 | 621 |
| Citric Acid Anhydrous | 900 | 835 | 828 | 828 | 835 |
| Sodium Carbonate | 585 | 621 | 621 | 621 | 621 |
| Potassium Bicarbonate | — | — | — | — | — |
| Docusate Sodium/Sodium Benzoate 85/15% | — | — | — | — | — |
| Colloidal Silicon Dioxide | 4 | 4 | — | — | 4 |
| Povidone | — | 17.5 | 17.5 | — | 8.750 |
| Total tablet weight | 3354.0 | 3378.5 | 3367.5 | 3350 | 3369.75 |
| Acid Neutralizing Capacity (ANC) | Not Determined | 12.3 | Not Determined | Not Determined | Not Determined |
| Acid to base ratio | 1:1.3 | 1:1.5 | 1:1.5 | 1:1.5 | 1:1.5 |
| Disintegration Time | — | <3 min | — | — | — |
| pH | — | 5.658 | — | — | — |

Sodium carbonate contributed to higher ANC and higher pH than sodium bicarbonate on an equivalent weight basis.

Slightly bigger tablets with a higher level of the effervescent couple gave better DT than smaller tablets with similar pH values, and increasing the acid to base ratio from 1:1.3 to 1:1.5 improved DT and increased ANC very slightly.

The tablets containing the surfactant, docusate sodium, showed prolonged disintegration with considerable foaming.

Overall, the low acid to base ratio prototypes with a lower pH did not lead to complete disintegration and dissolution of the ASA. Undissolved particles or agglomerates remained after the disintegration of the tablet mass in some cases.

Examples 15-31

Examples (Table 3) with higher acid to base ratios (1:2.05 to 1:5.9), exhibited relatively shorter disintegration times and higher pHs (>pH 6.4) than those with lower acid to base ratios. It is believed that the higher pH enhanced dissolution in the absence of the extra sodium ions to effect salt formation of ASA.

TABLE 3

(mg/effervescent tablet)

| Ingredients | Ex. 15 | Ex. 16 | Ex. 17 | Ex. 18 | Ex. 19 | Ex. 20 |
|---|---|---|---|---|---|---|
| ASA micronized, $D_{50}$ 10-25 micron | 800 | 800 | 800 | — | 800 | 800 |
| ASA micronized/Sodium Carbonate | — | — | — | 1067 | — | — |
| Ascorbic Acid | 480 | 480 | 480 | 480 | 480 | 480 |
| Calcined Sodium Bicarbonate | 1828 | 1828 | 1370 | 1370 | 1370 | 1770 |

TABLE 3-continued

| (mg/effervescent tablet) | | | | | | |
|---|---|---|---|---|---|---|
| Sodium Bicarbononate | — | — | — | — | — | — |
| Citric Acid Anhydrous | 480 | 480 | 300 | 300 | 300 | 300 |
| Sodium Carbonate | 400 | — | 400 | 133 | — | — |
| Potassium Bicarbonate | — | — | — | — | 400 | — |
| Docusate Sodium/Sodium Benzoate 85/15% | 15 | 15 | — | — | — | — |
| Colloidal Silicon Dioxide | 15 | 15 | — | — | — | — |
| Povidone | — | — | 17.5 | — | 17.5 | 17.5 |
| Dimethicone calcium silicate | — | — | — | — | — | — |
| Total tablet weight | 4018 | 3618 | 3367.5 | 3350 | 3367.5 | 3367.5 |
| Acid Neutralizing Capacity (ANC) | 25.53 | 18.62 | 20.0 | 19.9 | Not Determined | 19.1 |
| Acid to base ratio | 1:4.6 | 1:3.8 | 1:5.9 | 1:5.9 | 1:5.9 | 1:5.9 |
| Disintegration Time | ~6 min | ~6 min | <2 min | <2 min | <3 min | <2 mins |
| pH | 6.709 | 6.364 | 6.676 | 6.760 | 6.418 | 6.457 |

| Ingredients | Ex. 21 | Ex. 22 | Ex. 23 | Ex. 24 | Ex. 25 | Ex. 26 |
|---|---|---|---|---|---|---|
| ASA micronized, $D_{50}$ 10-25 micron | 800 | 800 | 800 mg | 800 | 800 | 800 |
| ASA micronized/Sodium Carbonate | — | — | — | — | — | — |
| Ascorbic Acid | 480 | 480 | 480 | 480 | 480 | 480 |
| Calcined Sodium Bicarbonate | 1370 | 1370 | 1370 | 1770 | 1370 | — |
| Sodium Bicarbononate | — | — | — | — | — | 1770 |
| Citric Acid Anhydrous | 480 | 480 | 480 | 300 | 30 0 | 300 |
| Sodium Carbonate | 400 | 400 | 400 | — | — | — |
| Potassium Bicarbonate | — | — | — | — | 400 | — |
| Docusate Sodium/Sodium Benzoate 85/15% | 1.750 | — | — | — | — | — |
| Colloidal Silicon Dioxide | — | — | 4.0 | 4.0 | 4 | 4 |
| Povidone | 1.750 | 17.50 | 17.5 | 8.750 | 17.50 | 17.50 |
| Dimethicone calcium silicate | — | — | — | 0.875 | — | — |
| Total tablet weight | 3533.5 | 3547.5 | 3551.5 | 3363.62 | 3371.5 | 3371.5 |
| Acid Neutralizing Capacity (ANC) | Not Determined | Not Determined | Not Determined | Not Determined | Not Determined | Not Determined |
| Acid to base ratio | 1:3.7 | 1:3.7 | 1:3.7 | 1:5.9 | 1:5.9 | 1:5.9 |
| Disintegration Time | <2 min | 1 min 30 sec | <2 min | Similar to Ex. 20 | >3 min | 4 min |
| pH | 6.488 | 6.438 | 6.436 | Similar to Ex. 20 | Not Determined | Not Determined |

| Ingredients | Ex. 27 | Ex. 28 | Ex. 29 | Ex. 30 | Ex. 31 |
|---|---|---|---|---|---|
| ASA micronized, $D_{50}$ 10-25 micron | 800 | 800 | 800 | — | 800 |
| ASA micronized/Sodium Carbonate | — | — | — | — | — |
| Aspirin USP (80 mesh) | — | — | — | 800 | — |
| Ascorbic Acid | 480 | 480 | 480 | 480 | 480 |
| Calcined Sodium Bicarbonate | 1770 | 1770 | 1770 | 550 | 1400 |
| Citric Acid Anhydrous | 300 | 300 | 300 | 670 | 670 |
| Sodium Carbonate | — | — | — | 821 | — |
| Potassium Bicarbonate | — | — | — | — | — |
| Docusate Sodium/Sodium Benzoate 85/15% | — | — | — | — | — |
| Colloidal Silicon Dioxide | 4 | 4 | 4 | 4 | 4 |
| Povidone | — | 17.50 | — | — | 17.50 |
| Dimethicone calcium silicate | — | — | — | — | — |
| Croscarmellose Sodium | — | 35 | — | — | — |
| Total tablet weight | 3389 | 3371.5 | 3354 | 3325 | 3371.5 |
| Acid to base ratio | 1:5.9 | 1:5.9 | 1:5.9 | 1:2.05 | 1:2.08 |
| Disintegration Time | Not Determined | Not Determined | Not Determined | Not Determined | >3 min |
| pH | Not Determined | Not Determined | Not Determined | Not Determined | 5.695 |

ANC values of the examples were relatively higher compared to the examples having lower acid to base ratios. Sodium carbonate contributed to the higher ANC more than sodium bicarbonate on an equivalent weight basis. Sodium carbonate also contributed to higher pH more than sodium bicarbonate on an equivalent weight basis.

The addition of the surfactant, docusate sodium, caused considerable foaming even at low levels.

Overall, the high acid to base ratio prototypes with the higher pH effected complete disintegration and dissolution of the ASA within 5 min.

Simulated Gastric Fluid Tests

Examples 32-35 were prepared having the compositions shown in Table 4. The acid neutralizing capacity (ANC) ranged from 13.2 to 18.2 mEq. The disintegration time was within 2 minutes±30 secs. The pH of the disintegration medium ranged from 6.1 to 6.5. In a simulated gastric fluid test, one tablet of each example was dissolved in 120 mL of HCL and the appearance and pH were determined. The pH ranged from 4.16 to 5.10, compared to 2 tablets of Aspirin® Plus C, which exhibited a pH of 4.4 in the simulated gastric medium.

TABLE 4

(mg/effervescent tablet)

| Ingredients | Ex. 32 | Ex. 33 | Ex. 34 | Ex. 35 |
|---|---|---|---|---|
| ASA micronized, $D_{50}$ 10-25 micron | 800 | 800 | 800 | 800 |
| Ascorbic Acid | 480 | 480 | 480 | 480 |
| Calcined Sodium Bicarbonate | 1200 | 1770 | 550 | 165 |
| Citric Acid Anhydrous | 480 | 300 | 670 | 488 |
| Trisodium Citrate | — | — | — | 620 |
| Sodium Carbonate | 400 | — | 821 | 748 |
| Colloidal Silicon Dioxide | 4 | 4 | 4 | 4 |
| Povidone | 17.50 | 17.50 | 17.50 | 17.50 |
| Total tablet weight | 3381.5 | 3371.5 | 3342.5 | 3322.5 |
| Acid to base ratio | 1:3.3 | 1:5.9 | 1:2.1 | 1:3.1 |
| Acid Neutralizing Capacity (ANC) | 17.3 | 18.2 | 13.2 | 14.3 |
| Disintegration Time | 2 min 21 sec | 2 min 27 sec | 2 min 18 sec | <2 min |
| Disintegration Solution pH | 6.38 | 6.53 | 6.24 | 6.06 |
| Simulated gastric fluid test (appearance and pH) | Clear solution, 4.64 | Clear solution, 5.10 | Slightly cloudy solution, pH 4.3 | Slightly cloudy solution, pH 4.16 |

Batch Preparation

Batches of tablets corresponding to the compositions shown in Table 4 were prepared by the following processes:

Weighing, Screening and Blending

Povidone and colloidal silicon dioxide ("CSD") were added to the ASA, screened and blended for 30 minutes in a 1 cubic foot twin blender (blending speed 24 rpm) prior to the addition of ascorbic acid, citric acid, heat treated sodium bicarbonate, and sodium carbonate. The blend was mixed for an additional 20 minutes. Alternatively, the order of addition was sodium carbonate, calcined sodium bicarbonate, screened ASA/povidone/CSD mixture, ascorbic acid, citric acid, and trisodium citrate.

Drying

The blends were transferred to a bin for drying. The blends were dried to a low percent relative humidity by passing compressed air thorough rod shafts placed in the blends overnight.

Compression

After drying, the blends were compressed using a Fette 1200i (20-station tablet press) equipped with 1-inch diameter upper punches and lower punches.

Target tablet weight±5%; Target tablet hardness: 60 to 90 N; Tablet speed 20,000/25,000 Tablets/hr; Fill-o-matic speed: 30-45 RPM; Permissible Punch Load: 80 kN; Main compression force MV kN: 30-55 kN; Tablet filling depth: 6.40, 7.00 mm; Tablet cylinder height main compression: 3.0-3.6 mm; Tablet cylinder height pre-compression: 3.00-5.10 mm Packaging Packaging was performed using a pouch machine (Siebler Pouch Machine (HM 1/90). Tablets were packaged in aluminum foil pouches.

Stability

It was observed from stability studies of Exs. 32-35 that a drop in ASA assay levels at 40° C./75% RH appeared to correlate with increasing amounts of sodium carbonate in the tablets. The rate and level of the degradant free salicylic acid also appeared to correlate with increasing amounts of sodium carbonate. Therefore, it was found that stability was enhanced in the absence of sodium carbonate.

Disintegration Time Studies

A series of experiments (Table 5) were performed with the commercially available APC by compressing it to double weight/double dose (6.4 g tablet containing 800 mg aspirin and 480 mg vitamin C) and compressing additional tablets with a reduced amount of effervescent couple (EC). It was observed that the DT became extended from the current 3 min to 4 min and >30 min (not fully disintegrated, large mass of particles still present) for the 25 and 50% EC reduction respectively at 15° C. These results demonstrated that the EC not only provides the effervescence of the dosage form but is critical to the disintegration of the tablet and dissolution of the ASA.

TABLE 5

| Ingredients | APC double dose/double weight (mg/tablet) | 25% EC reduction (mg/tablet) | 50% EC reduction (mg/tablet) |
|---|---|---|---|
| ASA | 800 | 800 | 800 |
| Ascorbic Acid | 480 | 480 | 480 |
| Effervescent couple (EC) | 5120 | 3840 | 2560 |
| Total tablet weight | 6400 | 5120 | 3840 |
| DT (min) @ 15° C. (N = 6) | 2:59 | 3:51 | >30 |

In addition, when the modified APC formulations are compared to an embodiment of the present invention (Table 6), having a lower amount of EC and tablet weight, the tablet of the present invention has a DT comparable to the much larger tablet having only a 25% reduction in EC, showing full disintegration within 5 minutes at 15° C. and 4 minutes at >20° C., which is typical temperature during routine testing in production. The significance of the present invention is particularly highlighted when compared with the tablet having a 50% reduction in EC, which has a larger tablet weight (3.8 g) and higher amount of EC than the embodiment of the present invention, yet the modified APC tablet did not fully disintegrate within 30 minutes.

TABLE 6

| Ingredients | Ex. 36 (mg/tablet) |
|---|---|
| ASA | 800 |
| Ascorbic Acid | 480 |
| Effervescent Couple (EC) | 2080 |
| Total tablet weight | 3376.5 |

TABLE 6-continued

| Ingredients | Ex. 36 (mg/tablet) |
|---|---|
| DT (min) @ 15° C. (N = 4) | 4:15 to 6:09 |
| DT (min) @20° C. (N = 4) | 3:11 to 4:22 |

Bioequivalence Studies

In order to measure the pharmacokinetic (PK) parameters of an effervescent tablet according to the present invention and confirm its bioequivalence with two tablets of the commercially available combination of aspirin and vitamin C (Aspirin® Plus C), a PK study was performed using Example 36 (see Table 6).

Standardized vitamin C intake is needed to reduce the variability not related to differences between products and therefore optimize the chance to detect differences between the test and reference product. It is important to minimize dietary related differences in baseline Vitamin C concentrations due to the following:

Vitamin C is stored in at least two body pools, the labile pool which is quickly occupied and emptied, and a stable pool, which is more slowly occupied and emptied. This as well as the saturable gastrointestinal absorption, and a concentration-dependent renal reabsorption cause non-linear Vitamin C pharmacokinetics, and a dose dependent elimination-half life.

When vitamin C and ASA are administered concurrently, urinary excretion of vitamin C increases. ASA has been found to reduce the absorption of vitamin C by about one third. Salicylate competes with vitamin C for acidic receptors in the leucocytes membrane and therefore inhibits its uptake into leukocytes.

Subjects entered a 7-day supplementation period (Days −9 to −3) with a daily intake of 400 mg vitamin C. On the evening of Day −3, subjects arrived at the site and entered a 2-day run-in period (Days −2 to −1) with a daily intake of 200 mg vitamin C. During the 48-hour PK sampling period, the dietary intake of vitamin C was limited to the vitamin C administered with the investigational products. Each treatment sequence was separated by a 2-day wash-out period with daily vitamin C intake of about 200 mg.

Figure 2:
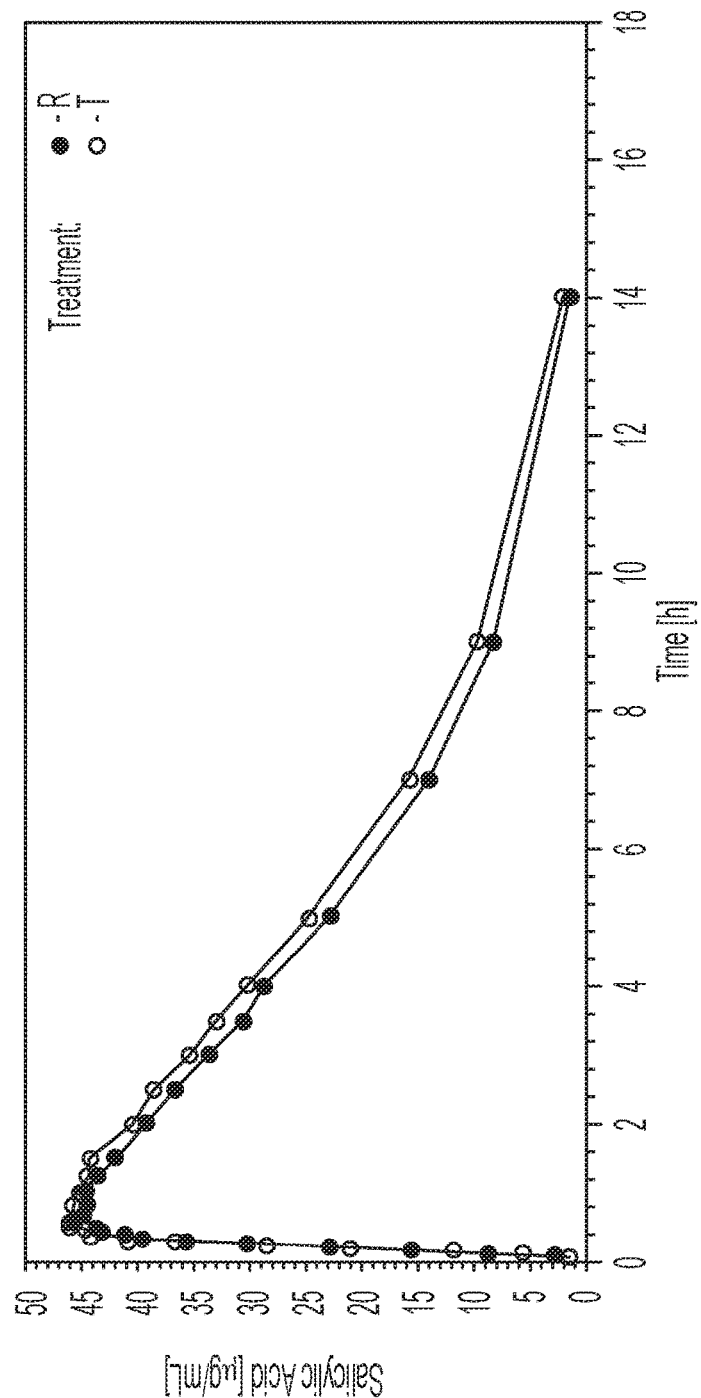
FIG. 2 is a chart showing mean plasma concentration of salicylic acid following administration of an effervescent tablet according to the present invention ("T") compared with the commercially available combination of aspirin and vitamin C (Aspirin® Plus C) ("R").
Figure 3:
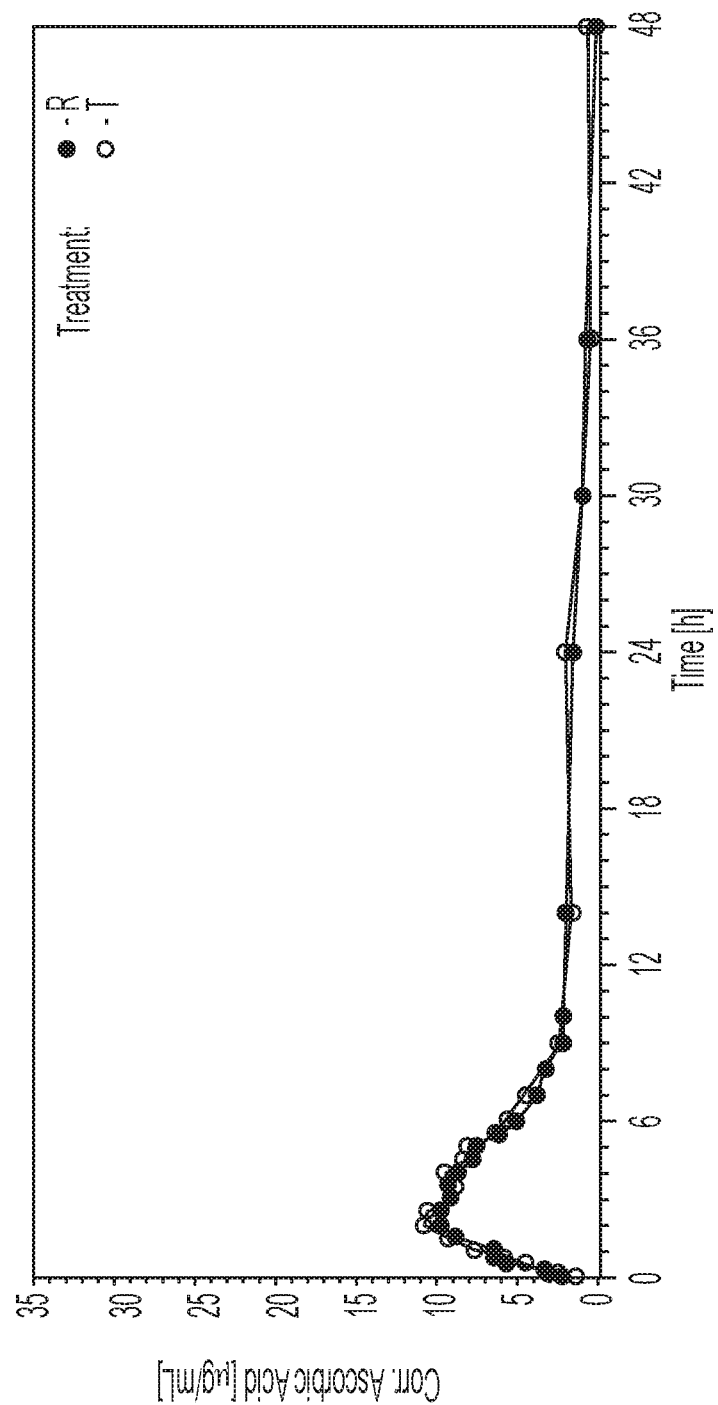
FIG. 3 is a chart showing mean plasma concentration of vitamin C following administration of an effervescent tablet according to the present invention ("T") compared with the commercially available combination of aspirin and vitamin C (Aspirin® Plus C) ("R").

FIGS. 1-3 illustrate the mean plasma concentrations of the analytes ASA, salicylic acid, and vitamin C, respectively, following administration of Ex. 36 ("Test") compared with two tablets of the commercially available combination of aspirin and vitamin C (Aspirin® Plus C) ("Reference"). The $C_{max}$, AUC, and $T_{max}$ were measured as follows in Table 8.

TABLE 8

| | ASA | | Salicylic Acid | | Vitamin C | |
|---|---|---|---|---|---|---|
| | Ex. 36 | Aspirin® Plus C | Ex. 36 | Aspirin® Plus C | Ex. 36 | Aspirin® Plus C |
| $C_{max}$ (μg/mL) | 28.2 | 28.1 | 50.8 | 50.8 | 13.4 | 12.2 |
| $AUC_{0-t}$ (μg · h/mL) | 11.6 | 12.6 | 276 | 257 | 123 | 123 |
| $AUC_{0-\infty}$ (μg · h/mL) | 12.0 | 12.9 | 285 | 264 | 138 | 137 |

TABLE 8-continued

| | ASA | | Salicylic Acid | | Vitamin C | |
|---|---|---|---|---|---|---|
| | Ex. 36 | Aspirin® Plus C | Ex. 36 | Aspirin® Plus C | Ex. 36 | Aspirin® Plus C |
| $T_{max}$ (min) | 16.8 | 15.0 | 30. | 34.8 | 150 | 150 |

Comparison demonstrates that Ex. 36 is bioequivalent with two tablets of the commercially available combination of aspirin and vitamin C (Aspirin® Plus C) with a high degree of confidence (see Table 9).

TABLE 9

| Analyte | Parameter | Ratio Test/Ref. | 90% CI |
|---|---|---|---|
| ASA | $C_{max}$ | 100.15% | 90.80-110.47% |
| | $AUC_{0-t}$ | 92.7% | 87.80-97.88% |
| Salicylic Acid | $C_{max}$ | 100.0% | 96.42-103.71% |
| | $AUC_{0-t}$ | 107.85% | 105.30-110.47% |
| Vitamin C | $C_{max}$ | 109.42% | 99.50-120.34% |
| | $AUC_{0-t}$ | 99.42% | 89.02-111.02% |

The purpose of the above description is to illustrate some embodiments of the present invention without implying a limitation. It will be apparent to those skilled in the art that various modifications and variations may be made in the apparatus or procedure of the invention without departing from the scope or spirit of the invention.

What is claimed is:

1. An effervescent tablet comprising
from about 600 to about 1000 mg of aspirin; and
from about 240 to about 600 mg of ascorbic acid; and
from about 1400 to about 2000 mg of alkaline substances, wherein the alkaline substances are selected from the group consisting of sodium bicarbonate, sodium carbonate, sodium citrate, and combinations thereof; and wherein the aspirin and alkaline substances are contained in a single layer.

2. The tablet according to claim 1, wherein the ascorbic acid is present in an amount of about 480 mg per tablet.

3. The tablet according to claim 1, comprising about 800 mg of aspirin.

4. The tablet according to claim 1, comprising about 800 mg of aspirin, about 1600 mg of alkaline substances, and about 480 mg of ascorbic acid.

5. The tablet according to claim 1, wherein the tablet dissolves in water in less than about 5 minutes.

6. The tablet according to claim 1, wherein the tablet has an acid neutralizing capacity of about 10 mEq to about 24 mEq.

7. The tablet according to claim 1, wherein the tablet has an acid neutralizing capacity of about 13 mEq to about 18 mEq.

8. The tablet according to claim 1, wherein the tablet has an acid neutralizing capacity of about 15 mEq.

9. The tablet according to claim 1, wherein the tablet is free of sodium carbonate.

10. The tablet according to claim 1, wherein the tablet has a weight of less than about 3600 mg.

11. The tablet according to claim 1, wherein the tablet has a thickness of not more than about 4.6 mm.

12. The tablet according to claim 1, wherein the pH of the tablet in an aqueous solution is about 5.8 to about 6.8.

* * * * *